(12) United States Patent
Ziaie et al.

(10) Patent No.: US 9,005,187 B2
(45) Date of Patent: Apr. 14, 2015

(54) METHOD AND APPARATUS FOR IMPROVING LOCAL HYPOXICITY FOR ENHANCED THERAPY

(75) Inventors: Babak Ziaie, West Lafayette, IN (US); Teimour Maleki, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 803 days.

(21) Appl. No.: 13/147,774

(22) PCT Filed: Feb. 3, 2010

(86) PCT No.: PCT/US2010/023037
§ 371 (c)(1),
(2), (4) Date: Aug. 3, 2011

(87) PCT Pub. No.: WO2010/091074
PCT Pub. Date: Aug. 12, 2010

(65) Prior Publication Data
US 2011/0295241 A1 Dec. 1, 2011

Related U.S. Application Data

(60) Provisional application No. 61/149,481, filed on Feb. 3, 2009.

(51) Int. Cl.
*A61B 18/14* (2006.01)
*A61B 18/06* (2006.01)
(Continued)

(52) U.S. Cl.
CPC . *C25B 9/10* (2013.01); *A61B 18/06* (2013.01); *A61B 2018/062* (2013.01);
(Continued)

(58) Field of Classification Search
CPC .............. C25B 1/04; C25B 9/10; C12M 1/00; C12M 3/00; A61M 37/00; A61M 1/00; C10B 25/00; C02F 1/46109; C02F 2209/22; A61N 1/32; A61N 1/44; A61N 1/18; A61N 1/0444; A61N 1/0436; Y02E 60/366; A61B 18/06; A61B 2018/062; A61B 2018/066
USPC .......................... 604/890.1, 891.1, 6.14, 6.16, 604/288.01–288.04
See application file for complete search history.

(56) References Cited

U.S. PATENT DOCUMENTS 7,498,275 B2    3/2009  Monzyk et al.
2001/0011645 A1*  8/2001  Silva et al. ............... 210/669
(Continued)

FOREIGN PATENT DOCUMENTS

WO    WO 2008091559 A1 *  7/2008  ............... A61N 1/20

OTHER PUBLICATIONS

Singh U.K., Middleton, R.H., Piezoelectric Power Scavenging of Mechanical Vibration Energy. (2007). Australian Mining Technology Conference, pp. 111-118.*
(Continued)

*Primary Examiner* — Ronald Hupczey
*Assistant Examiner* — Eunhwa Kim
(74) *Attorney, Agent, or Firm* — Ice Miller LLP (57) ABSTRACT

An implantable oxygen generator system is disclosed. The implantable oxygen generator system includes a receiver configured to generate an electrical current, and an electrode set configured to deliver the electrical current to water molecules of an interstitial fluid within a tissue, wherein the electrical current electrolyzes the water molecules into oxygen molecules.

18 Claims, 10 Drawing Sheets

(51) Int. Cl.
*C25B 9/10* (2006.01)
*A61N 1/32* (2006.01)
*A61N 1/44* (2006.01)
*A61N 1/04* (2006.01)
*C25B 1/00* (2006.01)
*C25B 1/02* (2006.01)
*C25B 1/06* (2006.01)
*C25B 1/10* (2006.01)

(52) U.S. Cl.
CPC ........ *A61B 2018/066* (2013.01); *A61N 1/0444* (2013.01); *A61N 1/0436* (2013.01); *C25B 1/00* (2013.01); *C25B 1/02* (2013.01); *C25B 1/06* (2013.01); *C25B 1/10* (2013.01); *A61N 1/32* (2013.01); *A61N 1/44* (2013.01); *Y02E 60/366* (2013.01)

(56) References Cited

U.S. PATENT DOCUMENTS

| | | | | |
|---|---|---|---|---|
| 2002/0017496 | A1* | 2/2002 | Kuriyama et al. | 210/748 |
| 2002/0022123 | A1* | 2/2002 | Bahar et al. | 428/306.6 |
| 2003/0087427 | A1 | 5/2003 | Colton et al. | |
| 2004/0133188 | A1* | 7/2004 | Vardi et al. | 604/891.1 |
| 2004/0238373 | A1* | 12/2004 | Kim et al. | 205/516 |
| 2006/0175195 | A1* | 8/2006 | Yamada et al. | 204/290.14 |
| 2007/0056847 | A1* | 3/2007 | Akahori et al. | 204/252 |
| 2010/0168646 | A1* | 7/2010 | Greenbaum et al. | 604/20 |

OTHER PUBLICATIONS

Parylene Engineering. (2010). Barrier Properties. Retrieved on Oct. 27, 2014 from http://www.paryleneengineering.com/barrier_properties_of_parylene.html.*

Arra, Satu, et al., "Ultrasonic Power and Data Link for Wireless Implantable Applications," IEEE 2007.

Bloch, Konstantin, et al., "Photosynthetic Oxygen Generator for Bioartificial Pancreas," Tissue Engineering, vol. 12, No. 2, 2006.

Daruwalla, Jurstine, and Christophi, Chris, "Hyperbaric Oxygen Therapy for Malignancy: A Review," World Journal of Surgery, (2006) 30: pp. 2112-2131.

Hausler, Rudolf, et al., "A Novel Implantable Hearing System with Direct Acoustic Cochlear Stimulation," Audiology & Neurotology, 2008; 13: pp. 247-256.

Li, Sheng-De, et al., "Water electrolysis in the presence of an ultrasonic field," Electrochimica Acta 54 (2009), pp. 3877-3883.

Maharbiz, Michel M., et al., "A Micorfabricated Electrochemical Oxygen Generator for High-Density Cell Culture Arrays," Journal of Microelectromechanical Systems, vol. 12, No. 5, Oct. 2003.

Neagu, Cristina, et al., "The electrolysis of water: an actuation principle for MEMS with a big opportunity," Mechatronics 10 (2000) pp. 571-581.

Oh, Se Heang, et al., "Oxygen generating scaffolds for enhancing engineered tissue survival," Biomaterials 30 (2009) pp. 757-762.

Ozeri, Shaul et al., "Ultrasonic transcutaneous energy transfer for powering implanted devices," Ultrasonics 50 (2010) pp. 556-566.

Pauwels, Ernest K.J. et al., "Assessment of Tumor Tissue Oxygenation: Agents, Methods and Clinical Significance," Drug News Perspect 20(10), Dec. 2007, pp. 619-626.

Rozenman, Yoseph, et al., "Wireless Acoustic Communication With a Miniature Pressure Sensor in the Pulmonary Artery for Disease Surveillance and Therapy of Patients with Congestive Heart Failure," Journal of the American College of Cardiology, vol. 49, No. 7, 2007, pp. 784-789.

Suzuki, Shin-nosuke, et al., "Power and Interactive Information Transmission to Implanted Medical Device Using Ultrasonic," Jpn. J. Appl. Phys, vol. 41 (2002), pp. 3600-3603.

Wu, Haiyan, et al., "In Situ Electrochemical Oxygen Generation with an Immunoisolation Device," Annals New York Academy of Sciences, date unknown, pp. 105-125.

* cited by examiner

FIG. 18

METHOD AND APPARATUS FOR IMPROVING LOCAL HYPOXICITY FOR ENHANCED THERAPY

PRIORITY

The present application is related to, claims the priority benefit of, and is a U.S. §371 national stage entry of, International Patent Application Serial No. PCT/US2010/023037, filed Feb. 3, 2010, which is related to, and claims the priority benefit of U.S. Provisional Patent Application Ser. No. 61/149,481, filed Feb. 3, 2009. The contents of each of these applications are hereby incorporated by reference in their entirety into this disclosure.

TECHNICAL FIELD

The present invention generally relates to cancer treatments and particularly as a method and apparatus for improving local hypoxicity of hypoxic tumors.

BACKGROUND

Cancer strikes millions of people every year. Currently, there are several ways of treating cancer. A successful treatment depends on many factors, including but not limited to the type of cancer, accessibility to the tumor, and to the progression of cancer in the body prior to start of the treatment. Two types of treatment are commonplace in treating cancer. The first is chemotherapy and the second is radiation therapy. Chemotherapy, which is defined as treatment of a disease by chemicals, generally operates by targeting cells that divide at a high rate. Rapid cell division is a characteristic of cancerous cells. In contrast to chemotherapy, radiation therapy, also referred to as radiotherapy, involves subjecting tumors to ionizing radiation. Treatment variables, e.g., dosage, duration, type of radiation therapy, depend on the type of tumor, the location of the tumor, how far the tumor has progressed, and the health of the patient.

Cancerous cells have distinct properties that are different than normal cells. As cancer progresses in a patient, the cancerous cells require more nutrients and oxygen as compared to cells of surrounding normal tissues. As a result, cancerous cells require rapid proliferation of new blood vessel networks, also referred to as tumor angiogenesis, to keep up with increased demands for nutrition, oxygen, and removal of cellular waste products. While a normal vasculature is characterized by an organized branching pattern of arteries, veins, and capillaries, tumor vessels are highly disorganized, and endothelial cells therein, i.e., cells that line the interior surface of blood vessels, do not form regular monolayers. As a result, the endothelial cells do not have a normal barrier function. These abnormalities as well other abnormal vascular structures, known in the art, result in tumor blood vessel leakiness. The leakiness causes a high interstitial fluid pressure within the tumor which causes tumor blood vessels to collapse and thereby impede blood flow. The collapse of the blood vessels is one reason why tumor tissue is usually hypoxic, i.e., lower than normal oxygen concentration, even though it is highly vascularized.

Tumor hypoxia can fundamentally impact the successes of both radiation therapy and chemotherapy in a negative manner. Hypoxic cells are resistant to cell killing treatments, e.g. by ionizing radiation. For example, it is well established that hypoxic tumor cells are 2-3 times more radio-resistant than normoxic cells, i.e., cells with normal oxygen concentration. Since tumor hypoxia can negatively impact chemotherapy as well as radiation therapy, several methods have been proposed to reduce tumor hypoxia as well as methods that take advantage of tumor hypoxia for targeted treatments of cancer tumors.

One proposal is to use drugs that are activated under hypoxic condition to selectively target hypoxic cancer cells. This drug treatment is especially important to hypoxic cancer tumors that do not respond to a conventional dose of radiation or chemotherapy. Tirapazamine is an experimental drug that is activated to a toxic radical when introduced to a hypoxic environment. Tirapazamine initially produced effective results with tolerable toxicity in patients with advanced head and neck cancers. However, the clinical development of tirapazamine was recently terminated due to unexpected toxicity observed in an international pharmaceutical trial.

Another proposal is to reduce hypoxic regions of an expanding tumor by normalizing leaky tumor vasculature. The normalization of leaky tumor vasculature is accomplished by using anti-angiogenic agents that inhibit tumor growth by preventing new vessel formation. However, there is a paradox with using anti-angiogenic agents to normalize leaky tumor vasculature. It has been hypothesized that anti-angiogenic therapy blocks the growth of blood vessels. As a result, the anti-angiogenic therapy should not increase the efficacy of chemotherapy or radiation therapy since these treatments require functioning blood vessels for drug and/or oxygen delivery. Therefore, when administering anti-angiogenic therapy, a balance has to be reached between improving the vasculature of tumors to enable more efficient delivery of drug and oxygen, and inhibiting tumor growth by preventing new vessel formation. The balance can be reached by judiciously administering the anti-angiogenic compounds.

Another proposal is to increase oxygen concentration in the body. Tumor oxygenation can be influenced by the arterial oxygen supply to the tissue which depends on the arterial $O_2$ and $CO_2$ content, and tissue perfusion. Higher tumor oxygenation can be accomplished by asking patients to breathe high oxygen content gases, which have been shown to improve oxygenation in several human tumors. Another way of increasing tumor oxygen concentration is by placing the patient in a hyperbaric oxygen therapy. An exemplary hyperbaric oxygen therapy includes deliver of 100% (or nearly 100%) oxygen at greater than 1 atmosphere in a chamber that completely encapsulates the patient. However, these enhanced oxygen therapies decrease the heart rate while maintaining the same stroke volume, which results in decrease cardiac output. At the same time, these enhanced oxygen therapies increase after-load through systemic vasoconstriction. The two effects can cooperatively intensify congestive heart failure in some patients. Other side effects include high fever, asthma, seizures and claustrophobia.

Therefore, there is a need to increase oxygen concentration inside or near a cancer tumor that does not suffer from the side effects of the above mentioned therapies.

SUMMARY

An implantable oxygen generator system is disclosed. The implantable oxygen generator system includes a receiver configured to generate an electrical current, and an electrode set configured to deliver the electrical current to water molecules of an interstitial fluid within a tissue, wherein the electrical current electrolyzes the water molecules into oxygen molecules.

A method for improving hypoxicity in an interstitial space for enhanced cancer therapy is also disclosed. The method includes implanting an implantable oxygen generator inside an interstitial space of a body, converting power from a power source to an electrical current, applying the electrical current to a liquid within the interstitial space to electrolyze water molecules in the liquid to generate hydrogen and oxygen molecules, the oxygen molecules diffuse into a hypoxic part of the interstitial space.

The described features and advantages, as well as others, will become more readily apparent to those of ordinary skill in the art by reference to the following description and accompanying drawings.

DETAILED DESCRIPTION

Figure 1:
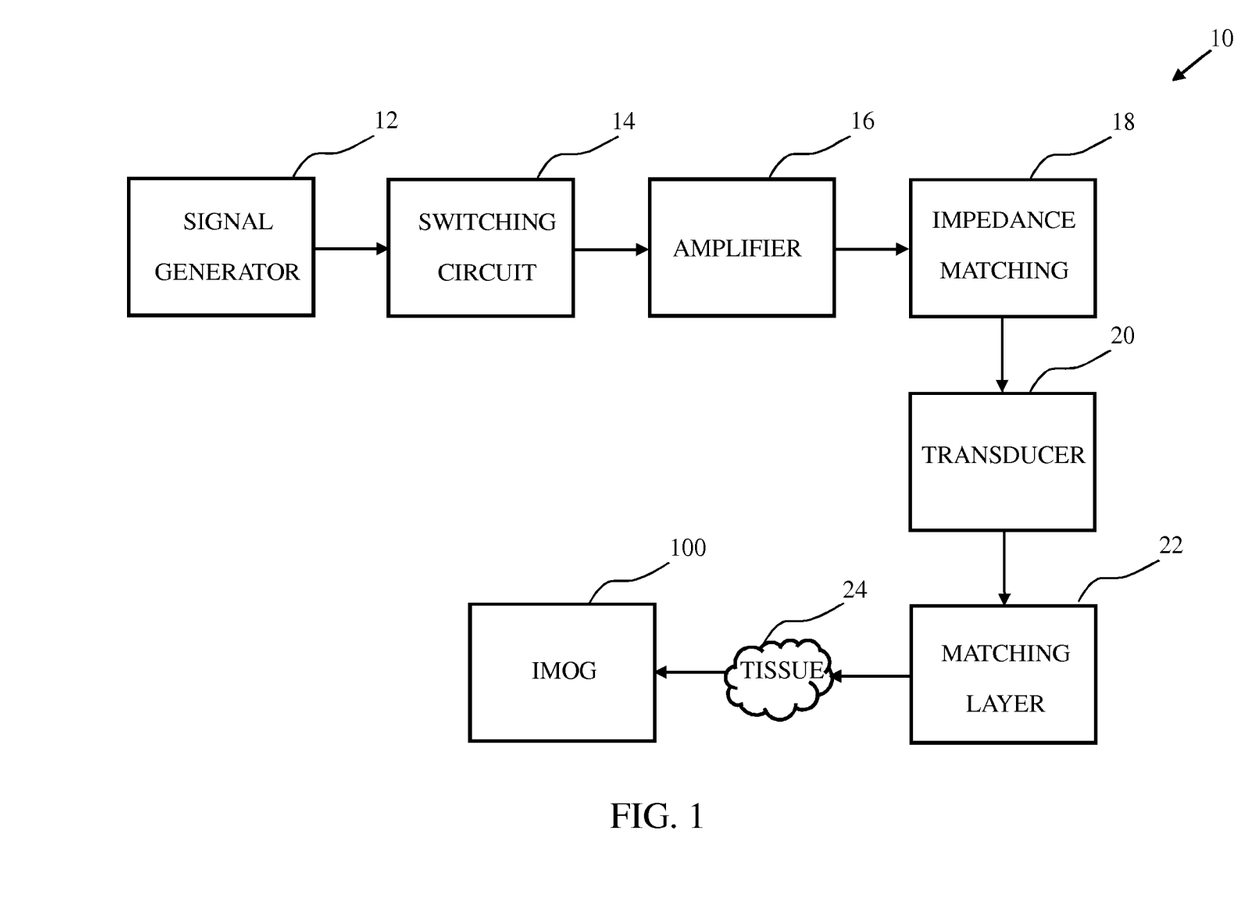
FIG. 1 depicts a block diagram of an implantable oxygen generator (IMOG) system including an IMOG device.

FIG. 1 depicts a block diagram of an implantable oxygen generator (IMOG) system 10. The IMOG system 10 includes a signal generator 12, a switching circuit 14, an amplifier 16, an impedance matching circuit 18, a transducer 20, a matching layer 22, a tissue 24, and an IMOG device 100. The signal generator 12, the switching circuit 14, the amplifier 16, the impedance matching circuit 18, the transducer 20, and the matching layer 22 are connected in series with each other. The series combination is connected to the IMOG device 100 through the tissue 24.

The signal generator 12, the switching circuit 14, the amplifier 16, the impedance matching circuit 18, the transducer 20, the matching layer 22 are components that provide power to and/or communicate with the IMOG device 100. The connection between the aforementioned components and the IMOG device 100 is via a wireless channel through the tissue 24.

The signal generator 12 generates a low power signal that is switched by the switching circuit 14. The switching circuit 14 generates a pulse train signal that is used as an excitation pattern for the transducer 20. The switching circuit 14 controls the on-time of the transducer 20. Due to high operational voltage and frequency at the transducer 20, power consumption of the transducer 20 results in overheating. To control the amount of heat that is generated by the transducer 20, the power is cycled according to the pattern generated by the switching circuit 14. Alternatively, the signal generator 12 is of a type capable of generating a pulse train, eliminating the need for the switching circuit 14.

The switched signal that is generated by the switching circuit 14 is amplified by the amplifier 16. The amplified signal is an amplified pulse train signal that is used to excite the transducer 20. However, prior to applying the amplified signal to the transducer 20, the impedances of the amplifier 16 and transducer 18 are matched by an impedance matching circuit 18, known in the art.

In particular, the goal of the impedance matching circuit 18 is to maximize power transfer from the amplifier 16 to the transducer 20 and minimize reflections from the transducer 20 back to the amplifier 16. In other words, the input impedance of the transducer 20 is matched to the output impedance of the amplifier 16. For varying signals, such as the pulse train pattern generated by the switching circuit 14, impedance of the transducer changes with frequency. The total impedance at the input of the transducer is a vector having a real part and an imaginary part. The real part is referred to as resistance R (measured in ohms, $\Omega$) and does not change with frequency. The imaginary part is referred to as reactance X (measured in ohms, $\Omega$), which is dependent on frequency. The impedance matching circuit 18 matches both the resistance as well as the reactance of the amplifier 16 and the transducer 20.

The transducer 20 converts the amplified and impedance matched pulse train signal to a power signal in the form of ultrasonic waves that can be absorbed by the tissue 24. The transducer 22 is a piezoelectric device, e.g., PSI-5-A4E (T140-A4E-602 of Piezo Systems, Inc.).

Prior to transmitting energy from the transducer 20 into the tissue 24, the energy is conditioned through a matching layer 22. The matching layer 22 is another impedance matching device that increases power absorption by the tissue 24 by minimizing reflection of the power signal bouncing off the tissue 24. Therefore, the matching layer 22 is a form of impedance matching.

The matching layer 22 is a mechanical member, e.g., a sheath, for conditioning the ultrasound waves transmitted from the transducer 20. The conditioned ultrasound waves are more effectively absorbed by the tissue 24 as a result of the matching layer 22, resulting in a more efficient power transfer. The thickness and mechanical properties of the matching layer 22 affect the power transfer. For example, a sheet of SU-8 2100 (Microchem, USA) was used over the transducer 20. The SU-8 2100 material a high contrast, epoxy based photoresist designed for micromachining and other microelectronic applications. It has an acoustic impedance of 3.4 M rayls. Sound impedance is the ratio between the sound pressure and a particle velocity the sound produces. The impedance is measured in rayls. The impedance is one rayl if a unit pressure of sound produces a unit velocity of a particle. The thickness of the matching layer 22 in the ultrasound power generation scheme is 311 µm for a target frequency of 2.3 MHz.

The target frequency of the transducer 20 is chosen to be same as resonant frequency of a transducer in the IMOG device 100. In order to maximizing power conversion by the IMOG device 100 using a wireless power transfer scheme, discussed below, the transducer 20 is operated at or near the resonant frequency of the transducer of the IMOG device 100. Also, in order to maximize power generation by the transducer 20, it may be also designed to have the same resonant frequency, i.e., 2.3 MHZ.

Once the power signal is absorbed by the tissue 24, the signal is transferred to the IMOG device 100. The IMOG device 100 receives the power signal and generates power from the power signal for its internal components, as will be described in greater detail below.

Figure 2:
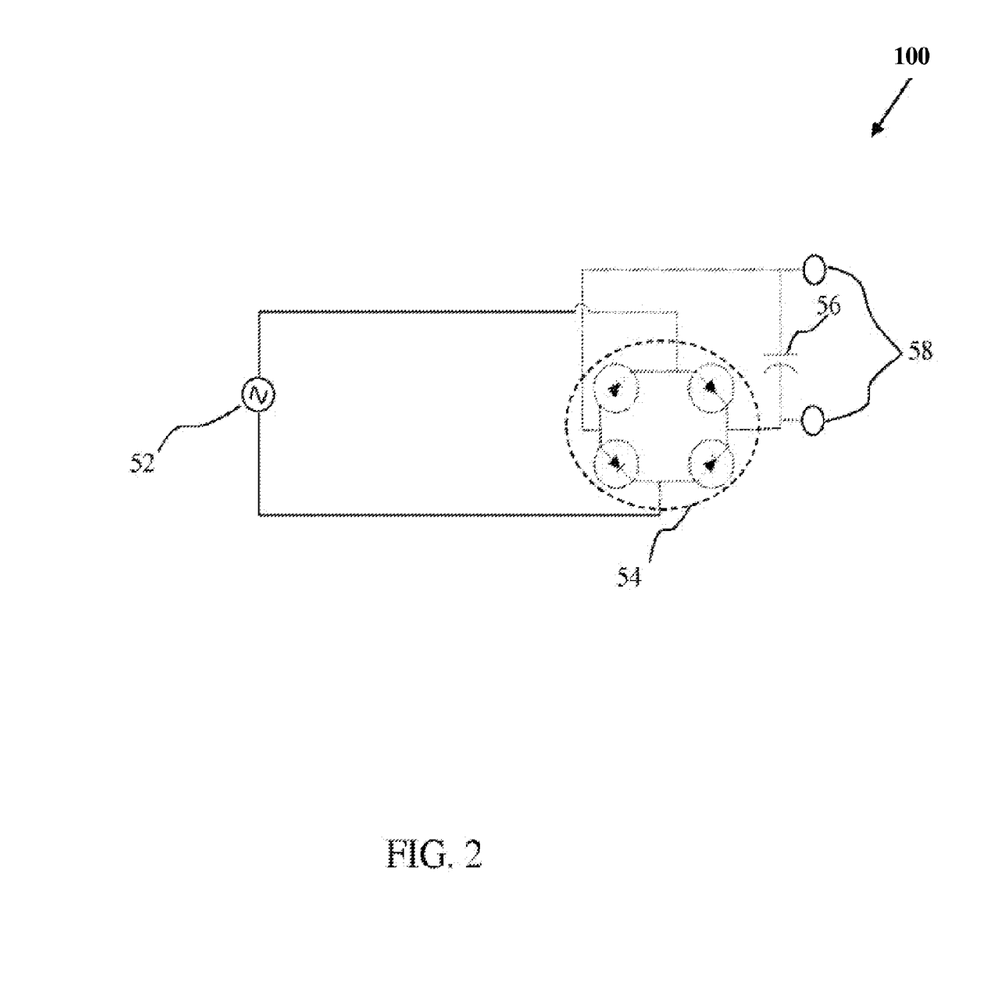
FIG. 2 depicts a schematic of the IMOG device of the IMOG system of FIG. 1.

FIG. 2 depicts an electrical schematic of the IMOG device 100. The IMOG device 100 includes a power generator 52, a rectifier bridge 54, a filtering capacitor 56, and output terminals 58. The power source 52 is serially connected to the rectifier bridge 54. The rectifier bridge is connected to the filtering capacitor 56. The combination of the rectifier bridge 54 and the capacitor 58 is connected to the output terminals 58.

The power source 52 is an ultrasonic transducer configured to convert ultrasonic energy that is transferred through the tissue 24 by the transducer 20 into an electrical current. The ultrasonic transducer 52 is a piezoelectric transducer. The piezoelectric transducer generates an AC (alternating current) type voltage with positive and negative components. The AC voltage is rectified by the full rectifier bridge 54, made up of diodes, into only positive voltage components. The capacitor 56 filters the rectified output into a semi-smooth pseudo-DC (direct current) voltage. The output of the capacitor 108 is provided to the output terminals 58.

Figure 3:
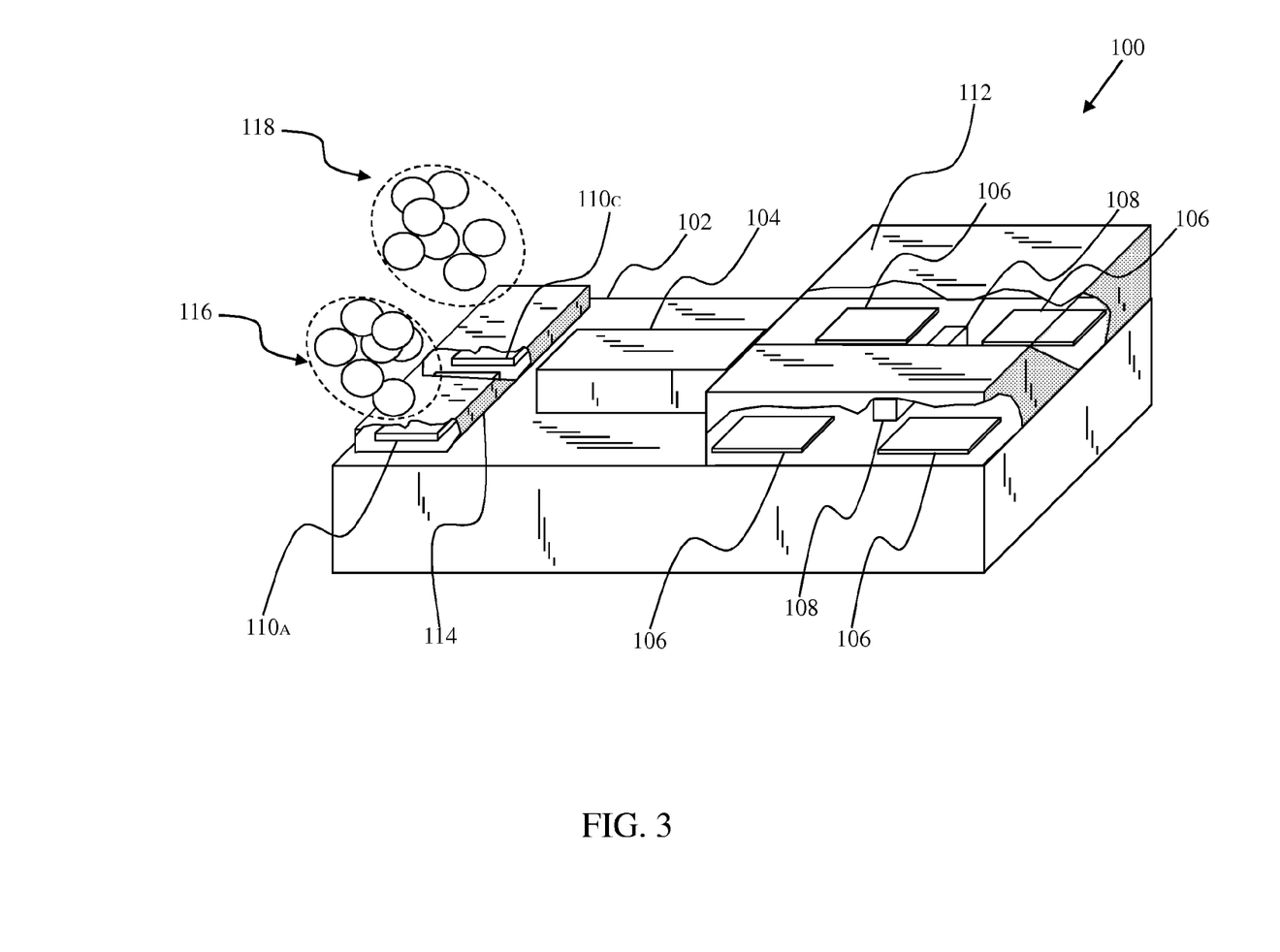
FIG. 3 depicts a perspective view of the IMOG device of the IMOG system of FIG. 1.

FIG. 3 depicts a perspective view of the IMOG device 100. The IMOG device 100 includes a substrate 102, a transducer 104, diodes 106, a capacitor 108, and electrodes $110_A$ and $110_C$. The electrode $110_A$ represents the anode and the electrode $110_C$ represents the cathode. The transducer 104, the diodes 106, the capacitor 108, and the electrodes $110_A$ and $110_C$ are disposed on the substrate 102. The transducer 104 is connected to a full rectifier bridge constructed by the diodes 106. The output of the rectifier bridge is filtered by the capacitor 108. The transducer 104 is a piezoelectric device for the ultrasonic power generation embodiment discussed above. The output of the capacitor 108 is connected to the electrodes $110_A$ and $110_C$. A protective layer 112 is disposed over the diodes 106 and the capacitor 108 to protect and electrically isolate these components during and after implantation of the IMOG device 100. An ion exchange membrane 114 is disposed over the electrodes $110_A$ and $110_C$ to prevent formation of chlorine gas and soda (NaOH), as discussed below. The IMOG device 100 also includes a bio-compatibility layer (not shown in FIG. 3) which is disposed over the entire device for reducing autoimmune rejection of the IMOG device 100.

The ultrasonic energy that is received by the IMOG device 100 impacts the transducer 104. As discussed above the combination of the rectifier bridge 210 and the filtering capacitor 212 provides a pseudo-DC voltage to the electrodes $110_A$ and $110_C$. The electrodes $110_A$ and $110_C$ conduct the filtered voltage to the water molecules surrounding the electrodes. An electrolysis reaction takes place when the electrodes $110_A$ and $110_C$ energize the water molecules and hydrogen ions. The hydrolysis reaction produces molecular hydrogen and oxygen gas.

Figure 4A:
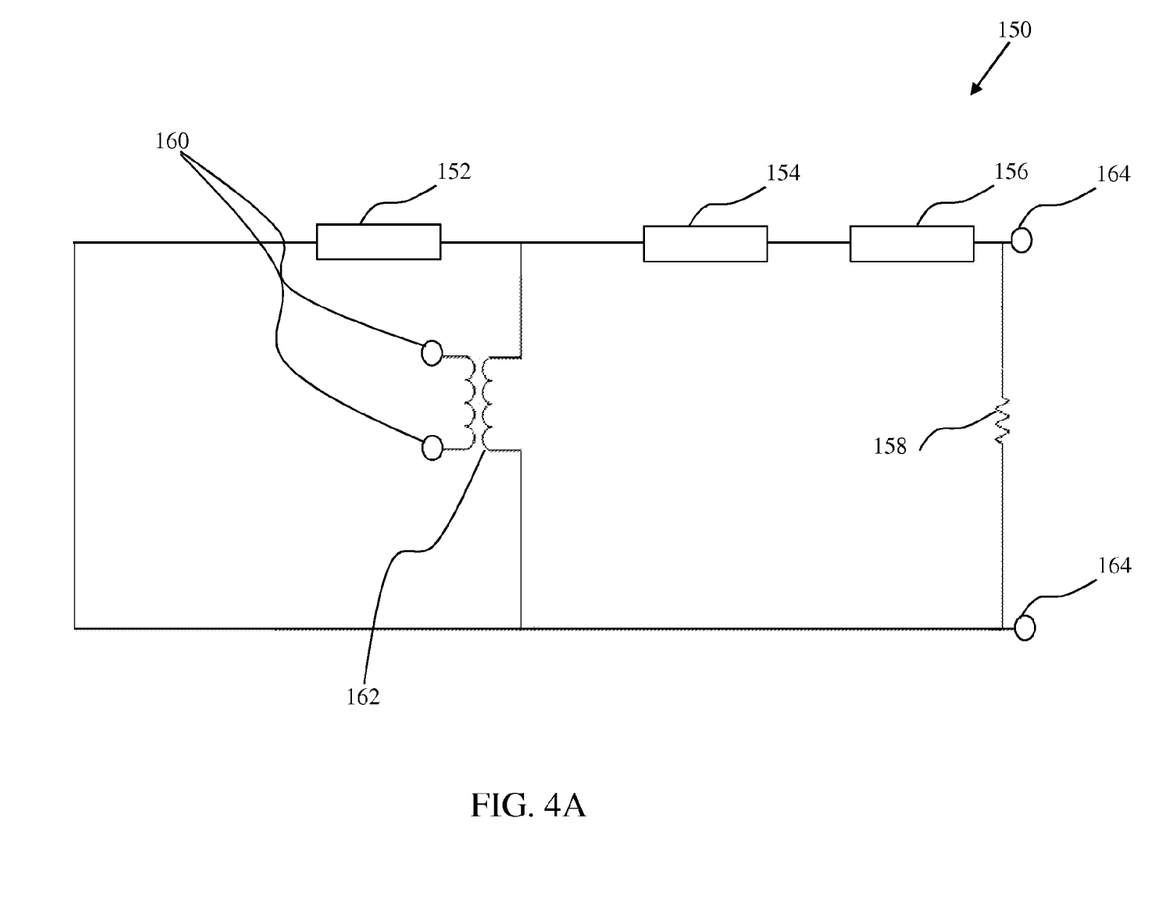
FIG. 4A depicts a schematic model of several components of a power generation scheme of the IMOG system of FIG. 1.
Figure 4B:
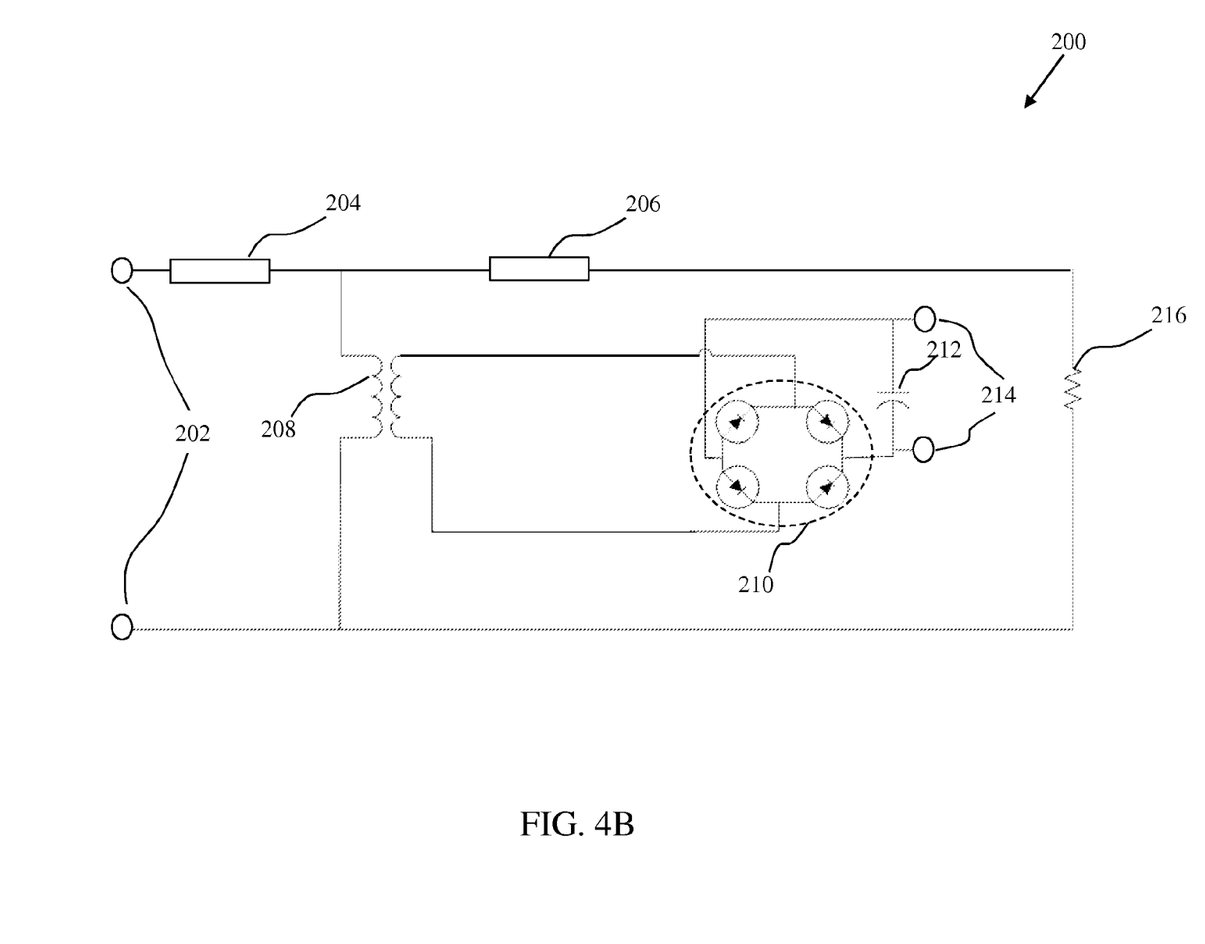
FIG. 4B depicts a schematic of an electromechanical model of the IMOG device depicted in FIG. 3.

In order to determine how much power is needed by the IMOG device 100 to perform the electrolysis reaction, and how much power must be generated at the transducer 20 to provide the necessary power to IMOG device using the wireless power transfer scheme, the models in FIGS. 4A and 4B were developed. FIG. 4A depicts a schematic model 150 of several components of the wireless power generation scheme of the IMOG system 10. The model 150 is primarily an acoustic model, starting at the transducer 20. In other words, the electrical components, e.g., the signal generator 12, the switching circuit 14, the amplifier 16, and the impedance matching circuit 18 are not modeled and therefore not depicted in FIG. 4A. The model 150 is referred to as a KLM model (after Krimholtz, Leedom and Matthae), which is commonly used in the bio-medical devices field to assist in designing high frequency transducers, such as a piezoelectric transducer.

A piezoelectric transducer is a device that converts an electrical current to mechanical vibration, and vice versa. The piezoelectric transducer has two mechanical ports and one electrical port. The mechanical ports can be modeled as input ports or output ports. For example, if the piezoelectric transducer is used as an electrical-to-mechanical transducer then both mechanical ports can be viewed as output ports. If however, the piezoelectric transducer is used as a mechanical-to-electrical transducer, then one or both of the mechanical ports can be viewed as an input mechanical port. Also, if a port is considered as input mechanical port, then it is connected to a mechanical source, and presents an input acoustic impedance. If however, the mechanical port is considered as an output mechanical port, then it is connected to an output mechanical load, and presents an output acoustic impedance. If an output port is free standing in air, then the output impedance of that port is very low. Therefore, if both output ports are free standing in air, then responsive to an electrical current, the piezoelectric may become hot, due to its mechanical vibration and its inability to transfer that vibration to a load.

The model 150 includes a modeled transducer 162 which is a piezoelectric transducer, configured to convert an electrical current to acoustic vibration. The modeled transducer 162 is a model representation of the physical transducer 20, depicted in FIG. 1. Since the piezoelectric transducer is used as an electrical-to-mechanical transducer, both mechanical ports are output ports that may be connected to respective loads. Each output port presents an output acoustic impedance that depends on its connection with the load. One of the mechanical output ports is free standing in air, which translates to a very low output acoustic impedance. The other mechanical output port is connected to the tissue (represented as 24 in FIG. 1), thereby presenting an output acoustic impedance.

The model 150 includes a transducer output acoustic impedance 152, a transducer output acoustic impedance 154, a matching layer output impedance 156, and a tissue load 158. The output acoustic impedance 152 is very low, since the respective output port is free standing in air, as discussed above. The model 150 further includes input terminals 160 for providing the input electrical current to the modeled transducer 162. In other words, the input terminals 160 represent the electrical side of the modeled transducer 162. The model 150 also includes output terminals 164 for providing acoustic power to the IMOG device 100, through the tissue 24, which generates a tissue load 158. The modeled transducer 162 is in parallel connection with the transducer output acoustic impedance 152 and the transducer output acoustic impedance 154. The transducer output acoustic impedance 154 is connected in series with the matching layer output impedance 156 which is connected to tissue load 158 and to the output terminals 164 in a parallel manner.

The transducer output acoustic impedance 152 and the transducer output acoustic impedance 154 are modeled based on a quarter wave length transmission line on each side of the transducer 120. Similarly, the matching layer output impedance 156 is also modeled based on a quarter wave length transmission line. The tissue load 158 is modeled as an acoustic impedance.

FIG. 4B depicts an electro-mechanical KLM model 200 of the IMOG device 100. The model 200 includes a modeled transducer 208 which is a piezoelectric transducer, configured to convert acoustic energy to an electrical current. The modeled transducer 208 is a model representation of the physical transducer 104, depicted in FIG. 3. Since the piezoelectric transducer is used as a mechanical-to-electrical transducer, one of the two mechanical ports is an input mechanical port that is connected to a mechanical input source, i.e. acoustic vibration transmitted through the tissue 24. The other mechanical port is an output mechanical port, since some of the vibrational energy is dissipated by the transducer 104 and some of the vibrational energy is transferred to the tissue 24. The mechanical input port presents an input acoustic impedance that depends on its connection with the source, i.e., vibrational energy transferred through the tissue. The mechanical output port presents an output acoustic impedance that also depends on its connection with the load, i.e., the tissue. Since both the input and output acoustic impedances of the input mechanical port and the output mechanical port are based on the connection with the tissue, these two impedance are substantially equal.

The model 200 further includes input terminals 202, transducer input acoustic impedance 204, transducer output acoustic impedance 206, full rectifier bridge 210, filter capacitor 212, output terminal 214, and a tissue load 216.

The modeled transducer 208 is in parallel connection with the transducer input acoustic impedance 204 and the transducer output acoustic impedance 206. The transducer output acoustic impedance 206 is connected in series with the tissue load 216.

The transducer input acoustic impedance 204 and the transducer output acoustic impedance 206 are modeled based on a quarter wave length transmission line on each side of the transducer 104. The tissue load 216 is modeled as an acoustic impedance. Unlike the KLM model depicted in FIG. 4A, the KLM model of the IMOG device 100, depicted in FIG. 4B, does not include a matching layer output impedance (156). This is because the IMOG device 100 was not equipped with a matching layer to match the acoustic impedance of the tissue. As a result, some acoustic reflection may take place off of the IMOG device 100, thereby reducing the efficiency of the IMOG device 100. However, a tissue-specific acoustic matching layer can be provided with the transducer 104 to improve the acoustic impedance matching between the piezoelectric transducer 104 and the surrounding tissue.

One of the uses of the models depicted in FIGS. 4A and 4B is to determine power efficiency. Power efficiency is defined as output electrical power of the transducer 104 to input electrical power of the transducer 20 (multiplied by 100). The power efficiency for the transducer 104 and the transducer 20 was determined to be about 0.1%. Once the power requirement of the IMOG device 100 is known, the power requirement of the transducer 20 can be determined based on the power efficiency. The power requirement of the transducer 20 is therefore dependent on the impedances discussed above (152, 154, 156, 158, 204, 206, and 216). Also, the impedances depend on the type of power transfer, i.e., ultrasonic, transducers, and tissue interface.

In order to determine power needed by the IMOG device 100, the following information was considered. A tumor size with a volume of about 3 cm$^3$ is used as a target size. In a typical tumor, interstitial fluid takes up about one sixth of the tumor volume. Therefore, the corresponding interstitial fluid in the target tumor has about 0.5 cm$^3$ (3/6=0.5 cm$^3$) of fluid. A normoxic tumor is oxygenated with about 50 mmHg partial pressure. In order to achieve this level of oxygenation, through empirical data, an oxygen concentration of 6.395×10$^{-5}$ mol/kg of oxygen was found to be needed. Therefore, in about 0.5 cm$^3$ of water (0.5 g), there should be about 3.197×10$^{-8}$ moles of oxygen. Each mole having 6.022×10$^{23}$ oxygen molecules (Avocado number), the required number of oxygen molecules in the tumor in order to achieve normoxicity is 6.022×10$^{23}$×3.197×10$^{-8}$=1.925×10$^{16}$. In order to determine how much electrical power is needed to generate 1.925×1016 oxygen molecules, the reaction at the electrodes 110$_A$ and 110$_C$ need to be considered.

At the electrode 110$_A$ (anode), a reaction according to formula (1), takes place:

$$2H_2O \rightarrow O_2 + 4H^+ + 4e^- \tag{1}$$

where H$_2$O is the water molecule,
O$_2$ is an oxygen molecule,
H$^+$ is an ionic form of a hydrogen atom, and
e$^-$ are electrons (4) needed for the reaction to take place. The oxygen molecules are depicted in FIG. 3 as a group of circles collectively identified as 116. Since 4 electrons are needed for each oxygen molecule that is released by the electrolysis reaction, 4 times 1.925×10$^{16}$ or 7.701×10$^{16}$ electrons are necessary to oxygenate the target tumor. Since there are 6.242×10$^{18}$ electrons in one Coulomb, the required number of electrons are equivalent to 12.32 mC. Using ten minutes as a target for an oxygenation therapy period, the required current is 20.5 μA (12.32 mC/10 min/60 seconds per min).

The minimum required voltage for the above electrolysis reaction is well documented to be 1.23 V. However, to ensure proper voltage levels, a voltage of 2.3 V was selected. Therefore, the power needed by the IMOG device 100 is 47.15 μW (2.3 V×20.5 μA). Since the power efficiency between transducers 104 and 20 was determined to be 0.1%, the electrical power needed at the transducer 20 is about 0.05 W. This level of input power at the transducer 20, which is easily achievable.

While the numbers above indicate power transfer between one transducer 120 outside the body and one transducer 104 of one IMOG device 100 inside an interstitial volume of a tumor, multiple IMOG devices 100 can also be used to improve power efficiency. For example, two IMOG devices implanted in the same interstitial volume of a tumor can improve the output efficiency from about 0.1% to about 0.2%.

Another reaction can also occur at the electrode 110$_A$ (anode). The interstitial fluid contains dissolved sodium (Na$^+$) and chloride (Cl$^-$) ions from naturally present salt, i.e., NaCl. As a result, performing water electrolysis would generate chlorine gases at the anode (in addition to the oxygen gas, discussed above) by oxidizing Cl$^-$ ions. The oxidation of Cl$^-$ ions is according to a reaction provided in formula (2), below.

$$2Cl^- \rightarrow Cl_2 + 2e^- \tag{2}$$

where Cl$^-$ are the free chloride ions,
Cl$_2$ is chlorine molecule in a gaseous form, and
e$^-$ are electrons (2) needed for the reaction to take place. The Cl$_2$ molecules are harmful to the body. The ion exchange membrane 114 disposed over the electrodes 110 (shown in FIG. 3) prevents Cl$^-$ ions from reaching the electrode 110$_A$ (anode), and thereby prevent formation of the chlorine gas.

While the discussion above is directed to the electrolysis reaction at the electrode 110$_A$ (anode), another reaction takes place at the electrode 110$_C$ (cathode). At the electrode 110$_C$ (cathode), a reaction according to formula (3), below, takes place:

$$2H^+ + 2e^- \rightarrow H_2 \tag{3}$$

where H$^+$ is the ionic form of a hydrogen atom,
e$^-$ are electrons (2) needed for the reaction to take place, and
H$_2$ is a hydrogen molecule. The hydrogen molecules are depicted in FIG. 3 as a group of circles collectively identified as 118. The hydrogen molecules are inert and do not oxidize by mammalian tissue even under hyperbaric conditions, discussed above. Eventually hydrogen molecules will be exhaled to atmosphere through lung tissues.

The overall interaction of Cl$^-$ and Na$^+$ ions in the electrolysis reaction, is shown below in formula (4), $$2NaCl + 2H_2O \rightarrow Cl_2 + H_2 + 2NaOH \tag{4}$$

where NaCl are salt molecules present in the interstitial fluid,
H$_2$O are water molecule present in the interstitial fluid,
Cl$_2$ are chlorine gaseous molecules, H$_2$ are hydrogen gaseous molecules, and
NaOH is sodium hydroxide (soda) molecules. The NaOH molecules are also harmful to the body. Therefore, the ion exchange membrane 114 prevents formation of both Cl$_2$ and NaOH.

The IMOG device 100 described above operates based on a wireless power transfer scheme using ultrasonic energy generated by the transducer 20 and received by the transducer 104 of the IMOG device 100. The wireless power generation scheme can be classified in a broad class of remote power transfer schemes to be contrasted with a broad class of local power generation scheme.

The class of remote power transfer includes both wireless power transfer as well as tethered power transfer. The wireless power transfer, as described herein, includes a power transmitter that generates a power signal which travels through the tissue to reach a companion IMOG device. However, in the tethered power transfer scheme, power is transferred to the companion IMOG device by a tether connected to the remote power source.

The broad class of local power generation scheme can be divided into three classes. In a first class, the IMOG devices are equipped with storage devices, e.g., a battery. In a second class, the IMOG devices use scavenging technologies, e.g., thermopile scavenging, and/or electrochemical scavenging to generate power at a slow rate and store the power in a storage device, e.g., a capacitor. In a third class, the IMOG devices generate power using radioactive seeds commonly used to treat certain kinds of cancer, e.g., the prostate cancer.

If the IMOG device is remotely powered, then the external components, enumerated in FIG. 1, provide power and communication signals to the IMOG device. If the IMOG device is powered by an internally stored power source, then the above enumerated components provide communication signals with the IMOG device 100. The communication signals in the latter case include instructions for power-cycling. The communication signals in both cases may include status/diagnostic information as well as therapy schedules.

Within the remote power generation class, there are several possible choices for transferring power to the companion IMOG device. While components of FIG. 1 are directed to an ultrasonic power generation scheme, a variety of other remote power generation schemes may also use the components that are depicted in FIG. 1. Examples of alternative remote power generation schemes are based on optical transmission, radiation-based transmission, magnetic, and audio based technologies.

In the sound power generation scheme, several of the aforementioned components in FIG. 1 are also used. However, the transducer 20 in the sound generation scheme is a speaker capable of producing sound, e.g., audible sound in the 20-20 KHz range. While a pulse train can result in pulsed sound waves generated by the speaker, a continuous signal can also be used to provide a continuous sounds wave. The companion IMOG device includes a transducer based that can vibrate in response to the produced sound. The vibration can be converted into an electrical current.

Furthermore, in the magnetic power generation scheme, the transducer 20 is a coil coupled to an antenna. The transducer produces a varying magnetic field that passes through the tissue. The transducer of the companion IMOG device is also a coil. The coil is configured to convert the varying magnetic field into an electrical current.

In the optical power generation scheme, the transducer 20 is an infrared transmitter, e.g., a bulb capable of generating high intensity infrared light. Similarly, the transducer of the companion IMOG device is a photodiode or a phototransistor. The photo diode is configured to convert light, e.g., focused infrared light, into an electrical current.

In the radiation-based power generation scheme, the transducer 20 is a radiation generator, e.g., used in radiation therapy, e.g., a linear accelerator used in accelerating ionic particles that are used in the therapy. The transducer in the companion IMOG device is a radiation diode that is used in remote or internal radiation based power generations schemes. The radiation diode is configured to convert high velocity ions striking the diode into an electrical current.

Figure 5:
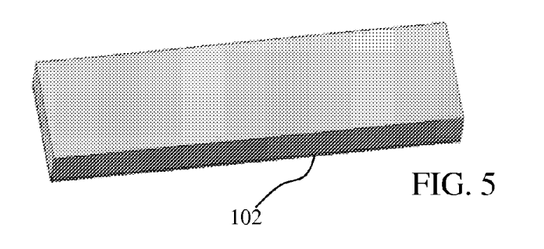
FIGS. 5 though 16 depict steps for fabricating the IMOG device depicted in FIG. 3.

FIGS. 5-16 depict exemplary steps in fabricating the IMOG device 100 of FIG. 3. The steps depicted in these figures can be performed by integrated circuit fabrication processes that are known in the art. FIG. 5 depicts the substrate 102. The substrate 102 can be the starting point for a wafer which will include multiple IMOG devices 100. Individual IMOG devices 100 can later be diced and singulated from the wafer. The substrate 102 is from a 300 µm thick glass wafer. Glass provides the least amount of parasitic capacitances that are formed between the enumerated components of the IMOG device 100, discussed above, in particular between the electrodes 100$_A$ and 100$_C$. Also, a glass substrate 102 eliminates the need for a passivation layer that is usually deposited over silicon substrates. The substrate 102 could also be a polymer such as polyimide to further reduce size of the substrate 102. Examples of other suitable substrate material for the substrate 102 are carbon, germanium, silicon carbide, Galium Arsenide, Indium Phosphide, and silicon germanium.

Figure 6:
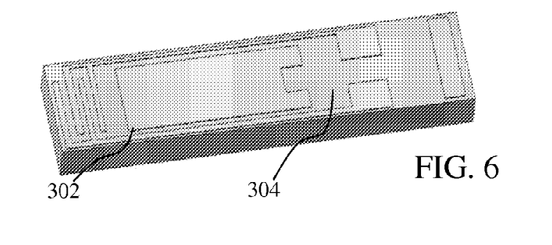

FIG. 6 depicts a metallization pattern formed after a metallization process. Using a lift off process, known in the art, contact metallization 302 is formed. Two metals, titanium and platinum at 400 Å and 1000 Å, respectively, were formed over the substrate 102. Titanium provides superior adhesion to the glass substrate. Other examples of methods of deposition are chemical vapor deposition and physical vapor deposition. The metallization layers 302 can alternatively be grown by an epitaxial growing process, or by a metal sputtering operation. Other examples of metallization material 302 are doped polysilicon, silver, gold, copper, tungsten, aluminum, iridium, ruthenium, and titanium nitride.

After the metallization process a layer of nitride 304 is deposited using a plasma enhanced chemical vapor deposition process, known in the art. The layer of nitride 304 behaves as an isolation layer which protects edges of the electrodes 110. In the absence of the isolation layer, titanium would be etched away electrochemically during the electrolysis reaction. For example, the electrodes 110 would be etched away in less than 10 minutes.

Figure 7:
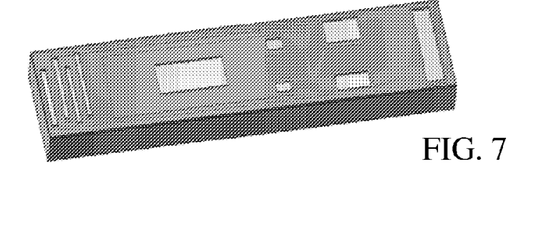

FIG. 7 depicts contacts after a contact forming process. A reactive ion etching (RIE) process, known in the art, is used to form the contacts, by etching away metallization metals that are not needed. Prior the RIE process, a photoresist patterning of the areas of the metal layers that are to be etched is processed. Once the photoresist pattern is placed, the RIE process removes unwanted metal layers, leaving only the contact areas.

Figure 8:
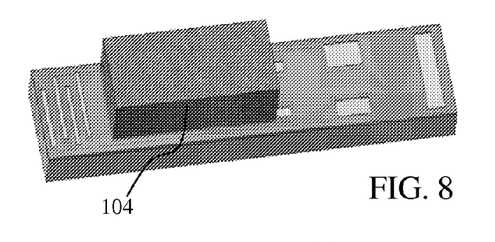

FIG. 8 depicts an intermediate state of the IMOG device 100 after formation of the transducer 104. A 1 mm thick, 5 mm long, and 1 mm wide Lead zirconate titanate (PZT, PSI-5A4E, Piezo Systems INC) sheet was attached to the substrate 102 using silver conductive ink (118-09 A/B, Creative Materials, USA) to form the transducer 104. The material and the size for the PZT were selected to provide an effective compromise between the size of the transducer 104 and ultrasonic body attenuation. In particular, the thinner the PZT sheet, the higher the resonance frequency, and hence the higher body attenuation, since the body attenuation increases by increasing the frequency. The material and the size of the transducer resulted in a resonance frequency of about 2.3 MHz.

Figures 9, 10:
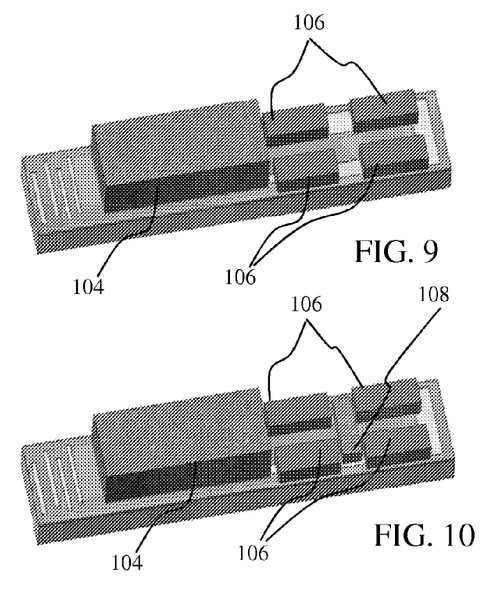

FIG. 9 depicts an intermediate state of the IMOG device 100 after bonding of the diodes 106 to the substrate 102. Four (4) Schottky barrier diodes (NSR0130P2T5G from ON Semiconductor) were bonded to the substrate 102. The diodes 106 are free of lead, considered a hazardous element for an implantable device. The diodes 106 have low forward voltages (0.25 V@ IF=500 µA), high reverse voltages (30V), fast switching speed, low reverse current (100 nA @ 15V), and small dimensions (0.95×0.36×0.55 mm3).

FIG. 10 depicts an intermediate state of the IMOG device 100 after bonding of the capacitor 108 to the substrate 102. The capacitor 108 is a 1 pF Multilayer Ceramic Chip Capacitor (C0603C0G1H010B from TDK). The capacitor 108 has a low equivalent series resistance, a high operational frequency, and a small dimension (0.5×0.3×0.3 mm3).

Figure 11:
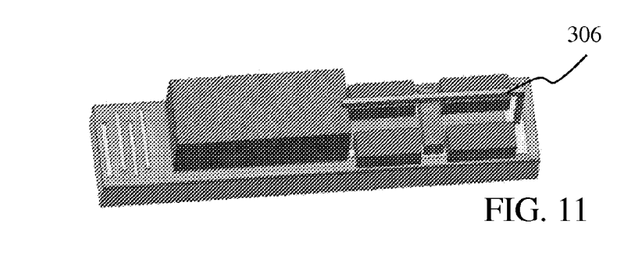

FIG. 11 depicts an intermediate state of the IMOG device 100 after forming a coupling wire 306 between the transducer 104 and the diodes 106. While one side of the transducer was connected to the rectifier bridge (formed of the diodes 106 and the capacitor 108), the other side was connected to the rectifier bridge using an external wire 306.

Figure 12:
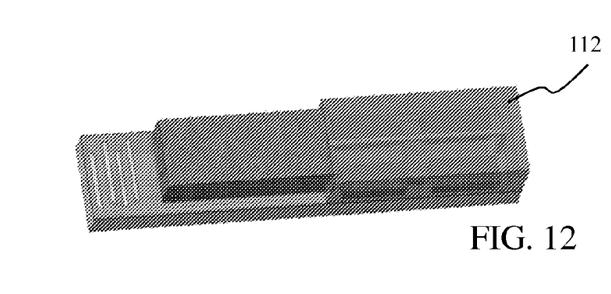

FIG. 12 depicts an intermediate state of the IMOG device 100 after forming the protective layer 112 over the diodes 106, the capacitor 108, and the external wire 306. The diodes 106, the capacitor 108, and the external wire were encapsulated with a Polydimethylsiloxane droplet. Polydimethylsiloxane belongs to a group of polymeric organosilicon compounds that is biologically inert, and therefore, suitable for implantable devices.

Figure 13:
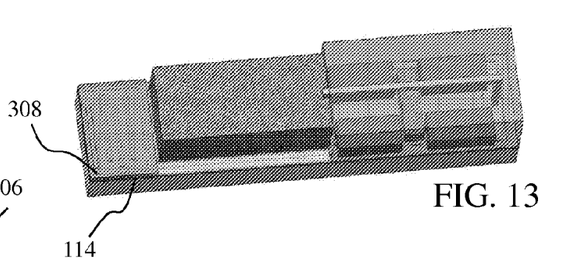

FIG. 13 depicts an intermediate state of the IMOG device 100 after formation of the ion exchange layer 114 over the electrodes 110. A layer of 100 µm thick CSO Selemion ion exchange membrane (AGC Engineering Co., Japan) was bonded over top of the electrodes 110 using a layer of epoxy. As discussed above, the ion exchange layer 114 is provided to block the chloride ions from reaching the electrodes. Absence of this layer can result in formation of chlorine gas from the free chloride ions in the interstitial fluid.

FIG. 13 depicts an intermediate state of the IMOG device 100 after treating the electrodes area with an adhesion promotion layer 308. The adhesion promotion layer promotes adhesion of a bio-compatibility layer 312 (FIG. 15) that is included in the entire IMOG device 100. A layer of AZ-174:DI water:IPA/1:100:100 was used as the adhesion promotion layer 308 to prevent liquid diffusion that would short the contacts.

Figure 14:
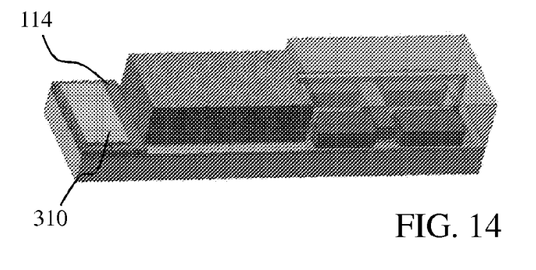

FIG. 14 depicts an intermediate state of the IMOG device 100 after photoresist patterning the ion exchange membrane 114. In order to prevent the bio-compatibility membrane 312 (FIG. 15) from entering the ion exchange membrane, thereby reducing its diffusivity, the ion exchange membrane 114 was patterned by a photoresist patterning process. FIG. 14 depicts a photoresist pattern layer 310 that is formed over the ion exchange membrane 114.

Figure 15:
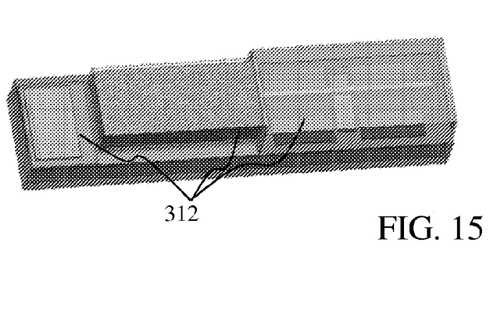

FIG. 15 depicts an intermediate state of the IMOG device 100 after formation of the bio-compatibility layer 312. The entire device is encapsulated by a five (5) µm thick parylene layer 312. The parylene layer is deposited using a chemical vapor deposition process.

Figure 16:
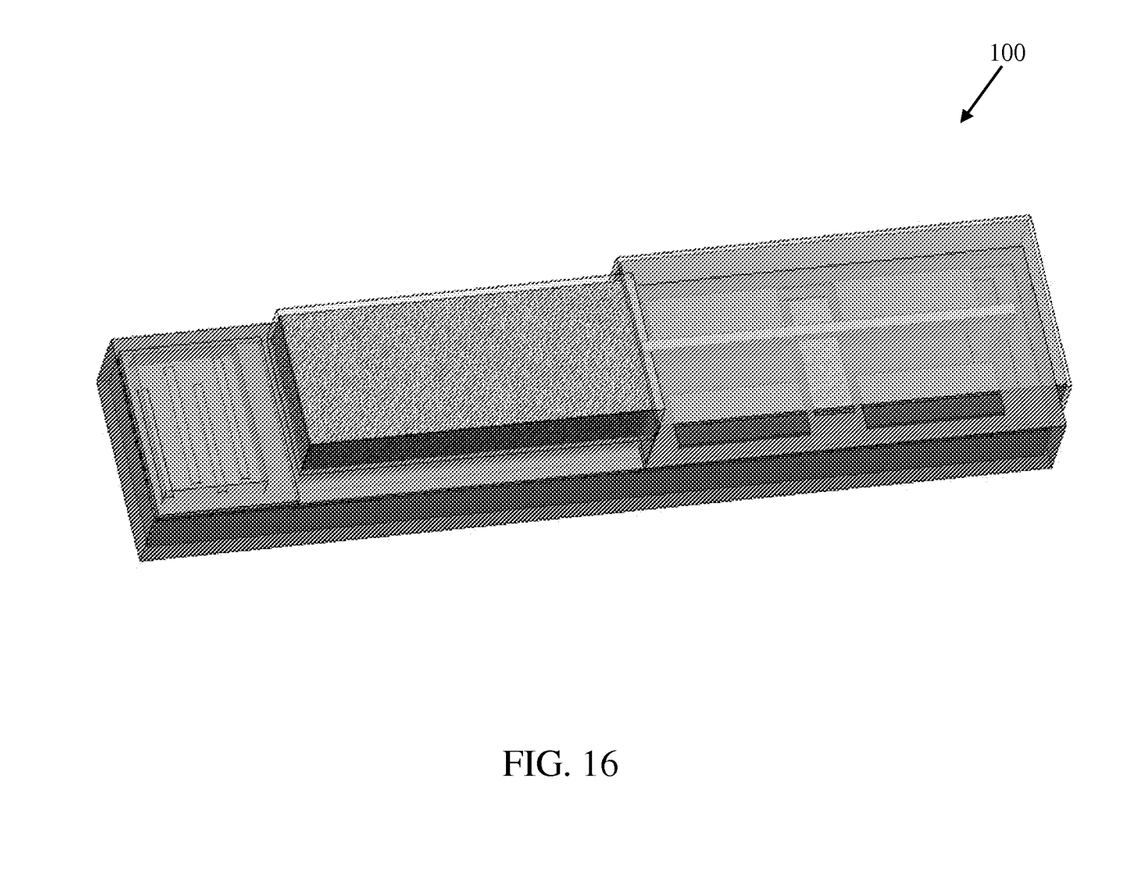

FIG. 16 depicts the fabricated IMOG device 100 after removal of parylene layer 312 from over the electrodes 110. After removal of the parylene layer 312, the photoresist was also removed by immersing the device in acetone.

The formation of the ion exchange membrane in the foregoing device fabrication steps is based on forming the membrane over the electrodes. However, it should be appreciated that the entire device may be encapsulated in the ion exchange membrane. In this alternative embodiment, the ion exchange membrane can take the place of the bio-compatibility layer 312.

Figure 17:
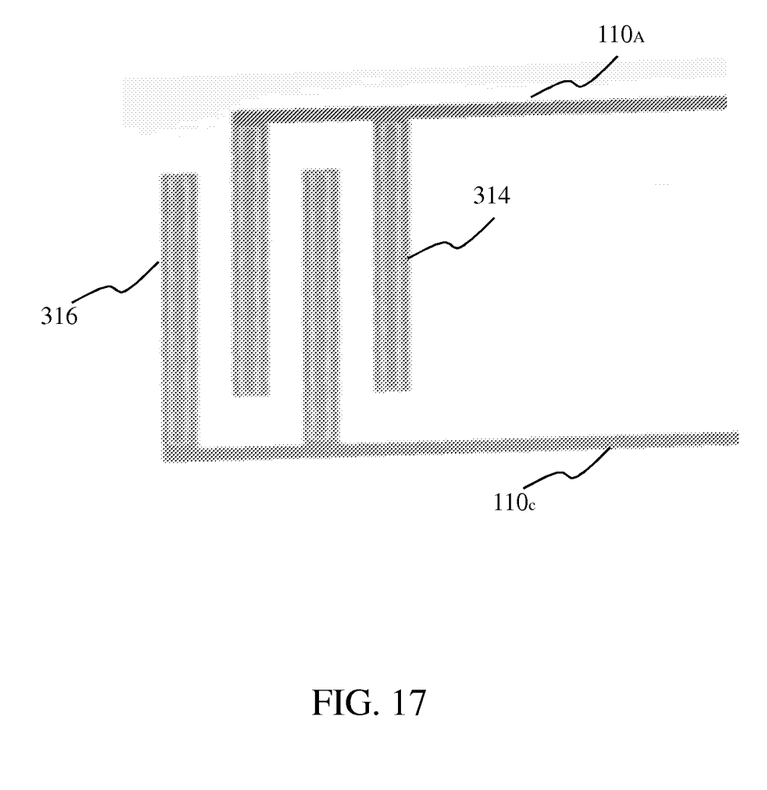
FIG. 17 depicts a fragmentary plan view of electrodes used in the IMOG device that is depicted in FIG. 3.

FIG. 17 depicts a fragmentary plan view of the electrodes $110_A$ and $110_C$. The electrodes $110_A$ and $110_C$ include fingers 314 and 316, respectively, to increase surface area of the electrodes. The increase in surface area improves the electrolysis reaction rate.

Figure 18:
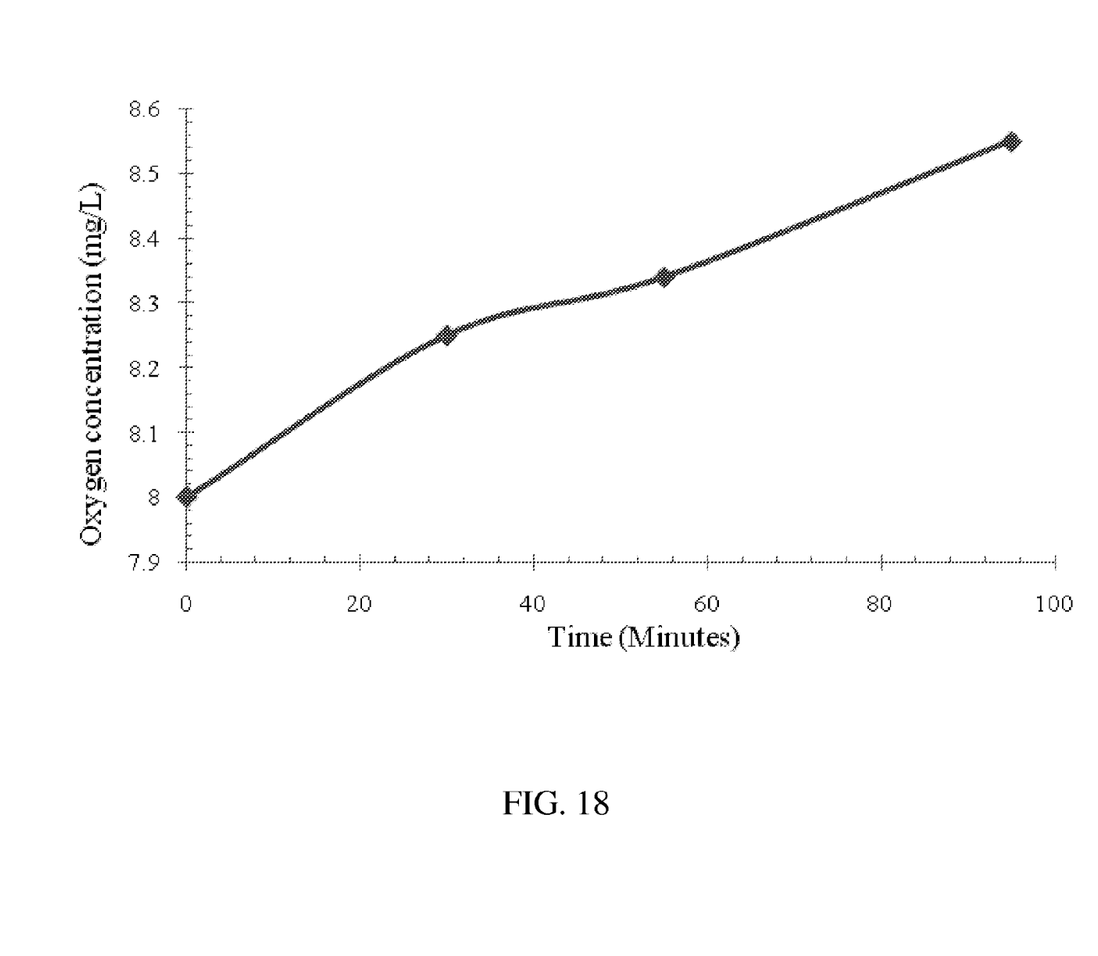
FIG. 18 depicts a graph of oxygen concentration vs. time when a current is passed through platinum electrodes that is encased with an ion exchange membrane.

FIG. 18 depicts a graph of oxygen concentration vs. time when a current is passed through platinum electrodes that is encased with an ion exchange membrane. The ion exchange membrane functionality of the IMOG device was verified by inserting two platinum coated electrodes covered by the ion exchange membrane in a flask partially filled with 200 mL of phosphate buffered saline (PBS 10%, from Sigma Aldrich, USA). A current of 1 mA was applied to the electrodes. Formation of oxygen was then monitored and recorded. The result of this validation experiment is shown in FIG. 18. The graph of FIG. 18 proves the membrane blocked formation of the chlorine molecules from chloride ions.

The IMOG device 100 can advantageously be used as a marker in a radiation therapy setting that is equipped with an imaging apparatus. Since tumors move, and since in radiation therapy, radiation beams use spatial targeting, it is advantageous to know where the tumor is located during the therapy. With that information, the radiation beams can continuously target the tumor.

Also, while not shown, the IMOG device 100 can be equipped with an anchoring feature, allowing it to be partially implanted in a tumor. Partial implantation is important for small tumors that may not be large enough for implanting an entire IMOG device 100.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

The invention claimed is:

1. An implantable oxygen generator system, comprising:
a receiver configured to generate an electrical current; and
an electrode set comprising an ion exchange membrane disposed over at least part of the electrode set, the ion exchange membrane configured to prevent formation of chlorine gas from free chlorine, ions in the interstitial fluid;
wherein the electrode set is configured to deliver the electrical current to water molecules of an interstitial fluid within a tissue, wherein the electrical current electrolyzes the water molecules into oxygen molecules at an average concentration of approximately 5.5 µg/L per minute, each electrode of the electrode set comprising an elongated stem and at least one finger extending from the elongated stem such that the at least one finger from one electrode is positioned adjacent to the at least one finger from the other electrode of the electrode set.

2. The implantable oxygen generator system of claim 1, the receiver further comprising:
an energy transduction circuit configured to receive energy from an energy source and generate an intermediate electrical current from the received energy;

a circuit configured to convert the intermediate electrical current into the electrical current.

3. The implantable oxygen generator system of claim 1, wherein the electrode set is plated with a plating material.

4. The implantable oxygen generator system of claim 3, the plated electrode set further comprising:
an isolation layer covering at least part of the plated electrode set, the isolation layer configured to protect the plated electrode set from etching by the plating material.

5. The implantable oxygen generator system of claim 3, wherein the plating material is one of platinum, gold, iridium oxide, carbon, titanium oxide, tungsten oxides, nickel-cobalt, nickel-iron, and zinc-nickel.

6. The implantable oxygen generator system of claim 1, the receiver further comprising a charge storage unit coupled to a transducer, wherein the charge storage unit is configured to store a trickling electrical charge over a period of time; and
a switching circuit coupled to the charge storage unit, wherein the switching circuit is configured to convert the stored electrical charge into the electrical current.

7. The implantable oxygen generator system of claim 1, the receiver further comprising:
an energy transduction circuit configured to receive energy from an energy source and generate the electrical current from the received energy, wherein the energy source is configured to generate one of a time varying energy output and a constant energy output.

8. A method for improving hypoxicity in an interstitial space for enhanced cancer therapy, comprising:
implanting a batteryless implantable oxygen generator inside an interstitial space of a body;
converting power from a power source to an electrical current;
applying the electrical current with an electrode set comprising an ion exchange membrane disposed over at least part of the electrode set to a liquid within the interstitial space to electrolyze water molecules in the liquid to generate hydrogen and oxygen molecules at an average concentration of approximately 5.5 µg/L per minute, the oxygen molecules diffuse into a hypoxic part of the interstitial space; and
preventing formation of chlorine gas from free chlorine ions present in the liquid when applying the electric current to the liquid.

9. The method of claim 8, further comprising:
providing power from an external power supply.

10. The method of claim 9, wherein the power supply is one of an optical generator, an ultrasound generator, a radiation generator, a sound generator, a magnetic generator, and a voltage generator.

11. The method of claim 8, further comprising:
providing power from an external power supply.

12. The implantable oxygen generator system of claim 6, the receiver further comprising one of:
an optical transducer configured to receive an optical energy from an external optical transmitter and to either (i) convert the received optical energy into the trickling electrical charge stored in the charge storage unit and convert the stored electrical charge into the electrical current by the switching circuit, or (ii) convert the received optical energy directly into the electrical current;
a piezoelectric transducer configured to receive an ultrasound energy from an external ultrasound transmitter and to either (i) convert the received ultrasound energy into the trickling electrical charge stored in the charge storage unit and convert the stored electrical charge into the electrical current by the switching circuit, or (ii) convert the received ultrasound energy directly into the electrical current;
a magnetic transducer configured to receive a magnetic field energy from an external alternating magnetic field generator and to either (i) convert the received magnetic field energy into the trickling electrical charge stored in the charge storage unit and convert the stored electrical charge into the electrical current by the switching circuit, or (ii) convert the received magnetic field energy directly into the electrical current;
an audio transducer configured to receive sound energy generated by an external speaker and to either (i) convert the received sound energy into the trickling electrical charge stored in the charge storage unit and convert the stored electrical charge into the electrical current by the switching circuit, or (ii) convert the received sound energy directly into the electrical current;
a radiation transducer configured to receive radiation energy generated by radiation seeds and to (i) convert the received radiation energy into the trickling electrical charge stored in the charge storage unit and convert the stored electrical charge into the electrical current by the switching circuit, or (ii) convert the received radiation energy directly into the electrical current; and
a heat transducer configured to receive body heat energy present in the interstitial fluid and to either (i) convert the received body heat energy into a trickling electrical charge stored in the charge storage unit and convert the stored electrical change into the electrical current by the switching circuit, or (ii) convert the received body heat energy directly into the electrical current.

13. An implantable oxygen generator system, comprising:
a wireless and batteryless receiver configured to generate an electrical current; and
an electrode set comprising an ion exchange membrane disposed over at least part of the electrode set, the ion exchange membrane configured to prevent formation of chlorine gas from free chlorine ions in the interstitial fluid;
wherein the electrode set is configured to deliver the electrical current to water molecules of an interstitial fluid within a tissue to electrolyzes the water molecules into oxygen molecules at an average concentration of approximately 5.5 µg/L per minute, the receiver comprising a transducer configured to receive power provided from outside of the tissue and convert the power to the electrical current.

14. The implantable oxygen generator system of claim 13, the receiver further comprising:
an energy transduction circuit configured to receive energy from an energy source and generate an intermediate electrical current from the received energy;
a circuit configured to convert the intermediate electrical current into the electrical current.

15. The implantable oxygen generator system of claim 13, wherein the electrode set is plated with a plating material and the plated electrode set further comprising:
an isolation layer covering at least part of the plated electrode set, the isolation layer configured to protect the plated electrode set from etching by the plating material.

16. The implantable oxygen generator system of claim 13, the receiver further comprising a charge storage unit coupled to the transducer, wherein the charge storage unit is configured to store a trickling electrical charge over a period of time; and a switching circuit coupled to the charge storage unit, wherein the switching circuit is configured to convert the stored electrical charge into the electrical current.

17. The implantable oxygen generator system of claim 13, the receiver further comprising:
an energy transduction circuit configured to receive energy from an energy source and generate the electrical current from the received energy, wherein the energy source is configured to generate one of a time varying energy output and a constant energy output.

18. The implantable oxygen generator system of claim 16, the receiver further comprising one of:
an optical transducer configured to receive an optical energy from an external optical transmitter and to either (i) convert the received optical energy into the trickling electrical charge stored in the charge storage unit and convert the stored electrical charge into the electrical current by the switching circuit, or (ii) convert the received optical energy directly into the electrical current;
a piezoelectric transducer configured to receive an ultrasound energy from an external ultrasound transmitter and to either (i) convert the received ultrasound energy into the trickling electrical charge stored in the charge storage unit and convert the stored electrical charge into the electrical current by the switching circuit, or (ii) convert the received ultrasound energy directly into the electrical current;
a magnetic transducer configured to receive a magnetic field energy from an external alternating magnetic field generator and to either (i) convert the received magnetic field energy into the trickling electrical charge stored in the charge storage unit and convert the stored electrical charge into the electrical current by the switching circuit, or (ii) convert the received magnetic field energy directly into the electrical current;
an audio transducer configured to receive sound energy generated by an external speaker and to either (i) convert the received sound energy into the trickling electrical charge stored in the charge storage unit and convert the stored electrical charge into the electrical current by the switching circuit, or (ii) convert the received sound energy directly into the electrical current;
a radiation transducer configured to receive radiation energy generated by radiation seeds and to (i) convert the received radiation energy into the trickling electrical charge stored in the charge storage unit and convert the stored electrical charge into the electrical current by the switching circuit, or (ii) convert the received radiation energy directly into the electrical current; and
a heat transducer configured to receive body heat energy present in the interstitial fluid and to either (i) convert the received body heat energy into a trickling electrical charge stored in the charge storage unit and convert the stored electrical charge into the electrical current by the switching circuit, or (ii) convert the received body heat energy directly into the electrical current.

\* \* \* \* \*